United States Patent
Maupin

(10) Patent No.: US 9,681,928 B1
(45) Date of Patent: Jun. 20, 2017

(54) ENDODONTIC ROTARY FILE SYSTEM HAVING SMALLER DIAMETER NON-LANDED FILES AND MEDIUM-TO-LARGER DIAMETER FILES WITH LANDED AND NON-LANDED PORTIONS

(71) Applicant: Charles Maupin, Lubbock, TX (US)

(72) Inventor: Charles Maupin, Lubbock, TX (US)

(*) Notice: Subject to any disclaimer, the term of this patent is extended or adjusted under 35 U.S.C. 154(b) by 359 days.

(21) Appl. No.: 14/341,964

(22) Filed: Jul. 28, 2014

Related U.S. Application Data

(63) Continuation-in-part of application No. 29/445,322, filed on Feb. 11, 2013, now Pat. No. Des. 710,009.

(51) Int. Cl.
*A61C 5/02* (2006.01)

(52) U.S. Cl.
CPC .................... *A61C 5/023* (2013.01)

(58) Field of Classification Search
CPC ........................................ A61C 5/023
See application file for complete search history.

(56) References Cited

U.S. PATENT DOCUMENTS

| | | | |
|---|---|---|---|
| 4,859,183 A | 8/1989 | Martin | |
| 5,092,769 A | 3/1992 | Reiter et al. | |
| 5,464,362 A * | 11/1995 | Heath | A61C 5/023 433/102 |
| 5,775,902 A | 7/1998 | Matsutani et al. | |
| 5,836,764 A | 11/1998 | Buchanan | |
| 6,174,165 B1 * | 1/2001 | Katsuumi | A61C 5/023 433/102 |
| 7,300,281 B2 | 11/2007 | Cantatore et al. | |
| 7,513,722 B2 | 4/2009 | Greenberg et al. | |
| 7,766,657 B2 | 8/2010 | Jaunberzins | |
| 8,047,842 B2 | 11/2011 | Johnson | |
| 8,137,101 B2 | 3/2012 | Fujii et al. | |
| 8,496,476 B2 | 7/2013 | Scianamblo | |
| 2010/0119990 A1 * | 5/2010 | Lampert | A61C 5/023 433/102 |
| 2013/0240092 A1 | 9/2013 | Gao et al. | |
| 2013/0273497 A1 | 10/2013 | Scianamblo | |

OTHER PUBLICATIONS

Rotary endodontic file for root canal desobturation PROTAPER® Universal Dentspl Y Maille Fer. Medical Expo. [Retrieved on Dec. 20, 2013]. Retrieved from the Internet: <URL:http://www.medicalexpo.com/prod/dentsply-maillefer/rotaryendodontic-files-root-canal-desobturation -72098 . . . >.

* cited by examiner

*Primary Examiner* — Heidi M Eide
(74) *Attorney, Agent, or Firm* — GableGotwals

(57) ABSTRACT

A set of at least three endodontic files, the first file of the set being entirely non-landed and tapered and having a diameter at its tip end which is smaller in diameter than that of a second and a third file of the set at their respective tip end, and the second and third files each having the following characteristics: a machined length, preferably 16 mm, having cutting surfaces thereon and starting at a tip end and extending less than the overall length of the file (preferably 25 mm); an active length starting at the tip end and extending to at least half of the machined length, the active length being tapered; a non-active length extending a remainder of the machined length, the non-active length being non-tapered; and the active length being landed in the first one-third and non-landed in the remaining two-thirds of its length.

14 Claims, 3 Drawing Sheets

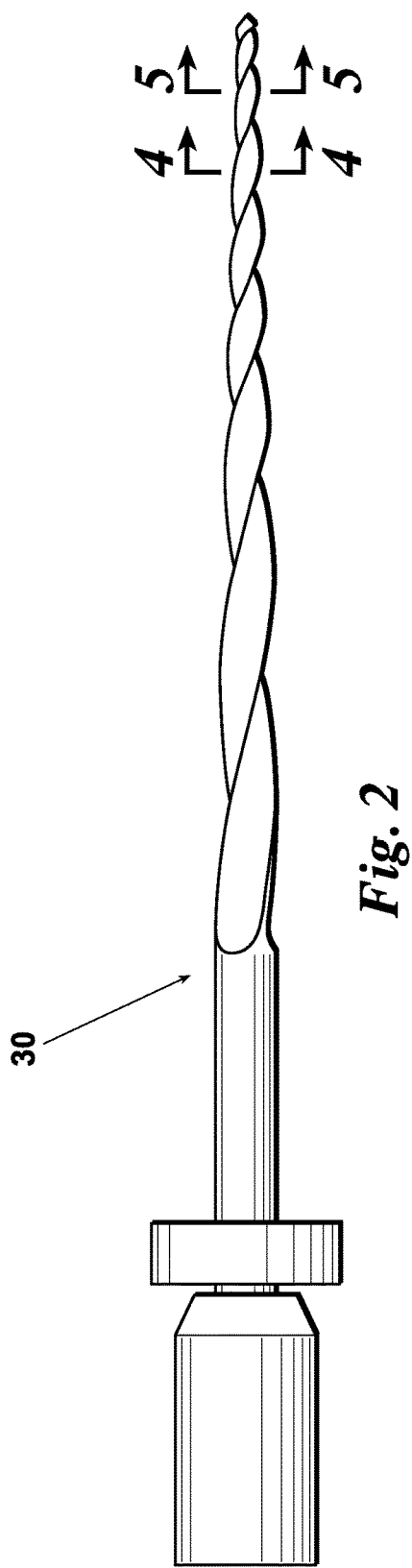
Fig. 2
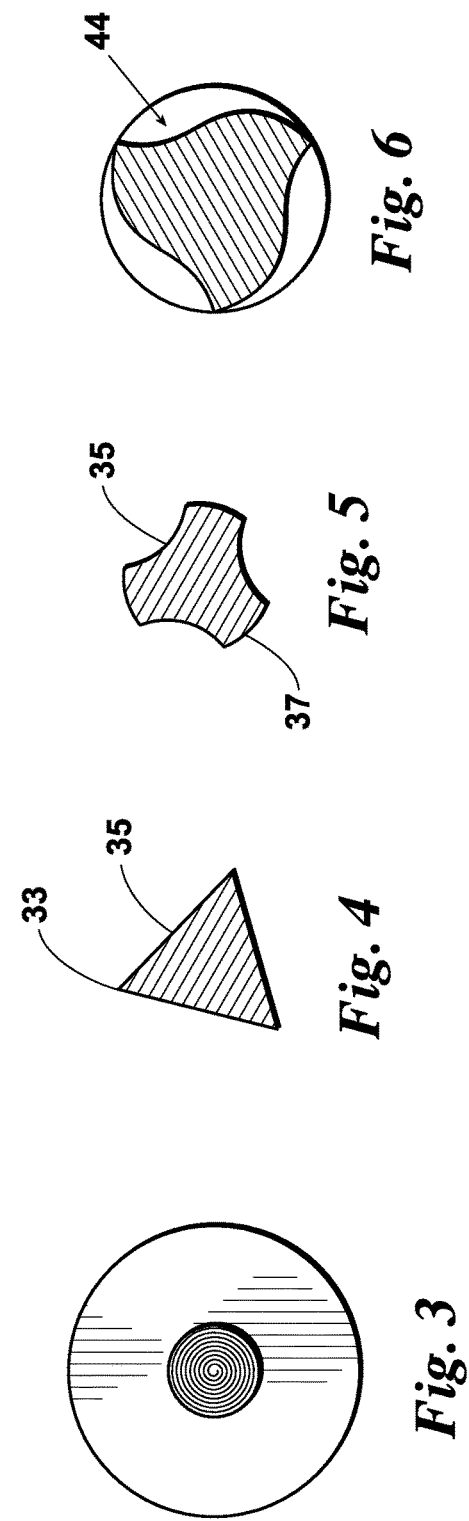
Fig. 6
Fig. 5
Fig. 4
Fig. 3

ENDODONTIC ROTARY FILE SYSTEM HAVING SMALLER DIAMETER NON-LANDED FILES AND MEDIUM-TO-LARGER DIAMETER FILES WITH LANDED AND NON-LANDED PORTIONS

CROSS-REFERENCE TO PENDING APPLICATIONS

This application claims priority to U.S. patent application Ser. No. 29/445,322 for Hybrid Rotary File, filed Feb. 11, 2013.

BACKGROUND OF THE INVENTION

All prior art endodontic file systems consist of either a landed rotary file or a non-landed rotary file. Landed rotary files are considered safer but less efficient than non-landed rotary files. Non-landed rotary files are considered more efficient but also more susceptible to procedural mishaps.

The radial lands of a landed rotary file keep the file centered in the root canal and help the file follow the natural canal anatomy. Therefore, when the file passes through the apical foramen of the canal, the file does not transport or destroy the natural apical anatomy. However, the file is less efficient at cutting because the radial lands prepare the canal in a planing motion. The landed file also has less flexibility leading to increased risk of file separation resulting in pre-mature loss of the tooth.

A non-landed file, while cutting more efficiently and having greater flexibility than a landed file, does not naturally stay centered in the root canal. Therefore, it can transport or straighten curved root canals. Further, when non-landed files of medium to large size (i.e., size 20 mm or greater) pass through the apical foramen of the canal, the files can transport the natural position of the apical foramen and rip the apical foramen. This transportation and ripping of the apical foramen leads to difficulty in filling the root canal and can lead to overfilling the root canal resulting in pre-mature tooth loss.

SUMMARY OF THE INVENTION

An endodontic system made according to this invention includes a set of at least three endodontic files, the first file of the set being entirely non-landed and tapered and having a diameter at its tip end which is smaller in diameter than that of a second and a third file of the set at their respective tip end, and the second and third files each having the following characteristics:
  a machined length, preferably 16 mm, having cutting surfaces thereon and starting at a tip end and extending less than the overall length of the file (preferably 25 mm);
  an active length starting at the tip end and extending to at least half of the machined length, the active length being tapered;
  a non-active length extending a remainder of the machined length, the non-active length being non-tapered; and
  the active length being landed in the first one-third and non-landed in the remaining two-thirds of its length.

The active length of the second is at least one of a different diameter at the tip end and a different taper than the third file. Preferably, the second and third files each have a diameter of at least 0.20 mm at the tip end and a taper of at least 4% along the active length. Beginning no sooner than 3 mm from the tip end, each file transitions from the landed portion to the non-landed portion.

An endodontic file made according to this invention has the same characteristics as the second and third file of the set.

BRIEF DESCRIPTION OF THE DRAWINGS

FIG. 2 is a side elevation view of the endodontic file of FIG. 1.

FIG. 3 is a top view of the file of FIG. 1.

FIG. 4 is a cross-section view taken along section line 4-4 of FIG. 2.

FIG. 5 is a cross-section view taken along section line 5-5 of FIG. 2.

FIG. 6 is a cross-section view as the file transitions between radial lands in the apical third of the file to no radial lands in the middle third.

FIG. 7 is a side elevation view of a first non-landed file, preferably a 15-04% non-landed file.

FIG. 8 is a side elevation view of a second non-landed file, preferably a 18-05% non-landed filed.

FIG. 9 is a side elevation view of a first landed and non-landed file, preferably a 20-06% file.

FIG. 10 is a side elevation view of a second landed and non-landed file, preferably a 25-04% file.

FIG. 11 is a side elevation view of a third landed and non-landed file, preferably a 30-06% file.

FIG. 12 is a side elevation view of a fourth landed and non-landed file, preferably a 40-06% file.

ELEMENTS AND NUMBERING USED IN THE DRAWINGS

Figure 1:
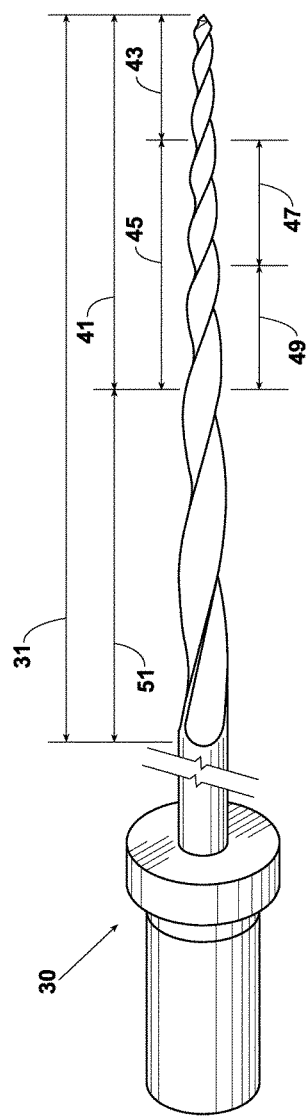
FIG. 1 is an isometric view of a preferred embodiment of an endodontic file made according to this invention. The file includes radial lands in the apical third portion of the file transitioning to no lands in the middle and coronal thirds of the file.
Figure 7:
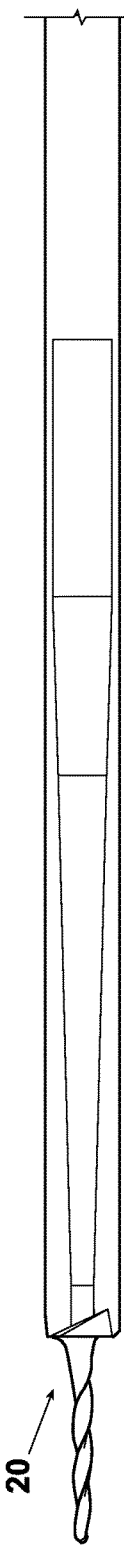
FIGS. 7-12 are preferred embodiments of a set of endodontic files for use in the system of this invention.
Figure 8:
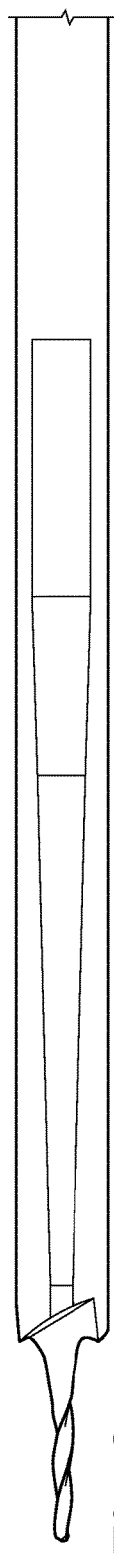
Figure 9:
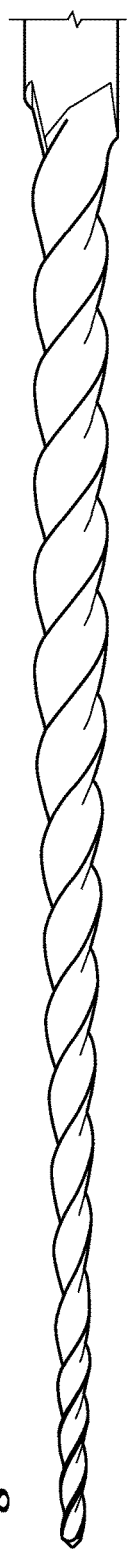
Figure 10:
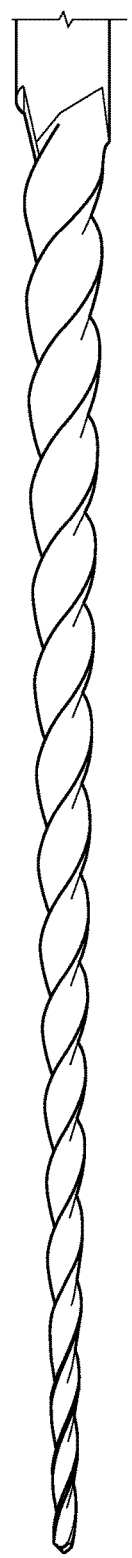
Figure 11:
Figure 12:

20 Non-landed file
30 "Hybrid" file
31 Machined length
33 Non-landed cutting surfaces or edges
35 Flutes
37 Radial lands or landed cutting surfaces
39 Tip end
41 Active length
43 Radial land portion of 41 or apical third
44 Transition between apical third 43 and middle third 47
45 Cutting length of 41
47 Middle third of 41
49 Coronal third of 41
51 Non-active length

DETAILED DESCRIPTION OF THE PREFERRED EMBODIMENTS

An endodontic system made according to this invention includes at least two different types of endodontic files. The first type of file is a non-landed file 20. The second type of file is a "hybrid" file 30, having radial lands in the apical third 43 of the active length 41 of the file 30 and being non-landed in the middle third 47 and coronal third 49, which form the cutting length 45.

Table 1 lists the preferred dimensions of the files 20 and 30 used in the system, with each hybrid file 30 preferably being 25 mm in overall length under the shank. The non-landed files 20 are of a kind well-known in the art. Preferably, there are two non-landed files 20 in the system 10, with each file 20 being less than 0.20 mm in diameter at its tip end and having less than a 6% taper.

The hybrid files 30 each include a tapered active length 41 and a non-tapered non-active length 51, the two lengths 41, 51 making up the overall machined length 31 of the file 30 (e.g. a 25 mm file 30 having a 16 mm machined length 31 of which 10 mm is the active length 41 and 6 mm is the non-active length 51). The apical third 43 of each file 30 is landed and extends to at least 3 mm from the tip end 39 of the file 30, depending on the active length 41. The cross section of apical third 43 is preferably formed by three flutes 35 with landed cutting surfaces or radial lands 37 in between (see FIG. 5).

The file 30 transitions between the radial lands 37 in the apical third 43 to no radial lands in the middle third 47 (see e.g. FIG. 6). This transition 44 occurs no sooner than 3 mm from the tip end 39. The cross section of the middle third 47 and coronal third 49 is preferably formed by three flutes 35 with non-landed cutting surfaces or edges 33 in between (see FIG. 4).

Preferably, there are four hybrid files 30 in the system having a minimum diameter at the tip end of no less than 20 mm and a tapered active length 41 of at least 4%, with each file 30 having a non-tapered non-active length 51. In one preferred embodiment, the four files 30 are sized 20-06%, 25-04%, 30-06%, and 40-06% respectively. The pitch of each file 30 preferably increases along the active length 41 toward the non-active length 51.

TABLE 1

Preferred Dimensions of the Endodontic Files Used in the System

| No. | Taper Active Length (%) | Slope Non-Active Length (%) | Radial Lands | Diameter (mm) | | | | Active Length (mm) | Progress pitch | | Machined Length (mm) |
| --- | --- | --- | --- | --- | --- | --- | --- | --- | --- | --- | --- |
| | | | | D0 | D3 | D10 | A | | At 0 mm | At 17 mm | |
| 15 | 4 | | No | 0.15 | | | | | | | |
| 18 | 5 | | | 0.18 | | | | | | | |
| 20 | 6 | 0 | Yes | 0.20 | 0.38 | 0.80 | 0.80 | 10.00 | 0.70 | 1.20 | 16 |
| 25 | 4 | | | 0.25 | 0.37 | 0.65 | 0.80 | 13.75 | | | |
| 30 | 6 | | | 0.30 | 0.48 | 0.80 | 0.80 | 8.33 | | | |
| 40 | 6 | | | 0.40 | 0.58 | 0.90 | 0.90 | 8.33 | | | |

Each hybrid file 30 combines the efficiency of a non-landed file with the safety of a landed file to provide a clinician with an efficient and safe file. The landed portion 43 of the file 30 helps the file 30 remain centered in the canal to maintain the original canal anatomy yet keeps the file 30 flexible due to the transition to a non-landed file in the middle third 47 and coronal third 49. When one or more files 30 are used in combination with non-landed files 20, the clinician has what he or she needs to successfully shape a patient's root canal without fear of file separation, strip perforation, transporting the canal or damaging the canal's apical foramen.

While the preferred embodiments have been described in detail, the invention is defined by the following claims, including those claims' full range of equivalency.

What is claimed is:

1. A set of endodontic files, the set including at least three files, the first file of the set being entirely non-landed and positive uniformly tapered toward a tip end and having a diameter at the tip end which is smaller in diameter than that of a second and a third file of the set at their respective tip end, the set further comprising:
   the second and third files each including
      a machined length having cutting surfaces thereon and starting at a tip end and extending less than the overall length of the file;
      a first length starting at the tip end and extending to at least half of the machined length, the first length being positive uniformly tapered toward the tip end;
      a second length extending a remainder of the machined length, the second length being non-tapered and being a same diameter as an uppermost end of the first length;
      the first length being landed in the first one-third of its length as measured from the tip end and non-landed in the remaining two-thirds of its length.

2. A set of endodontic files according to claim 1 further comprising the second and third files being a different diameter than one another at the tip end.

3. A set of endodontic files according to claim 2 wherein the second and third files each have a diameter in a range of 0.20 mm to 0.40 mm at the tip end.

4. A set of endodontic files according to claim 1 wherein the first length transitions to the non-landed portion no sooner than 3 mm from the tip end.

5. A set of endodontic files according to claim 1 wherein the machined length is 16 mm.

6. A set of endodontic files according to claim 1 further comprising a taper of the first length of the second file being a different taper than that of the first length of the third file.

7. A set of endodontic files according to claim 1 further comprising the non-landed portion of the first length including a triangular cross-section.

8. A set of endodontic files according to claim 1 further comprising the landed portion of the first length including a fluted cross-section.

9. An endodontic file comprising:
   a machined length having cutting surfaces thereon and starting at a tip end and extending less than the overall length of the file;
   a first length of the machined length starting at the tip end and extending to at least half of the machined length, the first length being positive uniformly tapered toward the tip end and including a triangular cross-section and a landed and a non-landed portion;

a second length extending a remainder of the machined length, the second length being non-tapered and being a same diameter as an upper most end of the first length.

10. An endodontic file according to claim 9 further comprising a diameter in a range of 0.20 mm to 0.40 mm at the tip end.

11. An endodontic file according to claim 9 wherein the machined length is 16 mm.

12. An endodontic filed according to claim 9 further comprising the first length being landed in a first one-third of its length as measure from the tip end and the non-landed portion being in a remaining two-thirds of its length.

13. An endodontic file according to claim 12 wherein the landed portion of the first length includes a fluted cross-section.

14. A set of endodontic files, the set including at least three files, a first file of the set being entirely non-landed and positive uniformly tapered toward a tip end and having a diameter at the tip end which is smaller in diameter than that of a second and a third file of the set at their respective tip end, the respective tip end of the second file being a different diameter than that of the third file;

the second and third files each including
- a machined length having cutting surfaces thereon and starting at the tip end and extending less than the overall length of the file;
- a first length starting at the tip end and extending to at least half of the machined length, the first length being positive uniformly tapered toward the tip end;
- a second length extending a remainder of the machined length, the second length being non-tapered and being a same diameter as an uppermost end of the first length;
- first length being landed in the first one-third of its length as measured from the tip end and including a fluted cross section and being non-landed in the remaining two-thirds of its length and including a triangular cross section;
- the first length further including a transitional cross section between the first one-third and the remaining two thirds.

\* \* \* \* \*